United States Patent
Doostdar et al.

(10) Patent No.: US 6,607,721 B2
(45) Date of Patent: Aug. 19, 2003

(54) METHODS AND COMPOSITIONS FOR CONTROLLING COLEOPTERAN INFESTATIONS

(75) Inventors: Hamed Doostdar, Ft. Pierce, FL (US); Richard T. Mayer, Ft. Pierce, FL (US)

(73) Assignees: The United States of America as represented by the Secretary of Agriculture, Washington, DC (US); Morse Enterprises Limited, Inc., Miami, FL (US)

( * ) Notice: Subject to any disclaimer, the term of this patent is extended or adjusted under 35 U.S.C. 154(b) by 0 days.

(21) Appl. No.: 10/136,379

(22) Filed: May 2, 2002

(65) Prior Publication Data

US 2003/0012771 A1 Jan. 16, 2003

Related U.S. Application Data

(62) Division of application No. 09/731,900, filed on Dec. 8, 2000, now Pat. No. 6,387,375.

(51) Int. Cl.[7] ............................................. A61K 35/84
(52) U.S. Cl. ................... 424/93.5; 424/195.15; 424/405; 435/254.1; 435/256
(58) Field of Search ................. 424/195.15, 195.16, 424/254.1, 254.7, 405, 931.1, 93.5; 435/41, 171, 254.1, 256; 504/101

(56) References Cited

U.S. PATENT DOCUMENTS 5,516,513 A    5/1996   Wright

FOREIGN PATENT DOCUMENTS

WO    WO 01/79450    10/2001

OTHER PUBLICATIONS

Michailides et al., "Transmission of Mucor–piriformis to Fruit of Prunus–Persica by Carpophilus spp and Drosophila–melanogaster", Plant Dis, 1990, 74 (4), 287–291, abstract.*

Dillard et al., "Transmission of Alternaria brassicicola to Cabbage by Flea Beetles (Phyllotreta cruciferae)", Plant Disease, Feb. 1998, vol. 82, No. 2, pp. 153–157, abstract.*

Rodriguez–Del–Bosque et al., "Effect of Ear Wounding and Cultural Practices on Abundance of Carpophilus freemani (Coleoptera: Nitidulidae) and Other Microcoleopterans in Maize in Northeastern Mexico", J of Econ Ent, Aug. 1998, 91 (4), 796–801, abstract.*

Bilbushnikova & Isangladin, "Determining biological activity of insecticides–using pupae of housefly as test object which is infected and counting dead images," Database WPI Week 199707, Derwent Publications Ltd., London, GB; AN 1997–075700 XP002192542 & RU 2 059 369 C (Appl Microbiolog Res Inst), May 10, 1996, Abstract.

Chuck Woods, "Diaprepes!", Impact; The University of Florida Institute of Food and Agricultural Sciences, pp. 10–11, Fall 2000.

Monica Lewandowski, "Citrus Growers and Scientist Tackle the Diaprepes Root Weevil", *Citrus & Vegetable Magazine*, Jan. 1999, pp. 6–8.

S.H. Futch et al., "2000 Citrus Pest Management Guide: Citrus Root Weevils", *Citrus and Vegetable Magazine*, Nov. 2000, pp. 6–8.

Windels et al., "Association of Fusarium SPP with Picnic Beetle on Corn Ears", *Phytopathology, 1976, 66(3), p. 328–331*.

Hara et al., "The Biology of the Black Twig Borer Xylosandrus Compacdtus in Hawaii USA", *Proc Hawaii Entomol Soc.*, 1979, 23(1), pp. 55–70.

Wells et al., "Toxigenic Species of Penicillium, Fusarium, and Aspergillus from Weevil–Damaged Pecans", *Can J. Microbiol.*, Feb., 22, 1976 (2):281–5.

* cited by examiner

*Primary Examiner*—Leon B. Lankford, Jr.
*Assistant Examiner*—Ruth A. Davis
(74) *Attorney, Agent, or Firm*—Banner & Witcoff, Ltd.

(57) ABSTRACT

Species of fungi have been identified, which can be used to control coleopteran infestations of host plants. The fungi are particularly useful for controlling infestations of *Diaprepes abbreviatus*.

38 Claims, 15 Drawing Sheets

(13 of 15 Drawing Sheet(s) Filed in Color)

METHODS AND COMPOSITIONS FOR CONTROLLING COLEOPTERAN INFESTATIONS

This application is a division of application Ser. No. 09/731,900, filed Dec. 8, 2000, now U.S. Pat. No. 6,387,375, which is incorporated by reference herein.

TECHNICAL FIELD OF THE INVENTION

This invention relates to fungi that are useful for controlling infestations of Coleoptera, particularly *Diaprepes abbreviatus*.

BACKGROUND OF THE INVENTION

A temperate climate provides a favorable environment for year-round cultivation of a variety of horticultural crops. The same mild conditions and the constant availability of host plants, however, also encourage the proliferation of herbivorous insects, including Coleoptera such as beetles and weevils. Significant crop damage will result if the population of these insects is not kept under control.

One such economically important pest is the sugar cane rootstalk borer Coleoptera, *Diaprepes abbreviatus* (Insecta: Coleoptera: Curculionidae). Diaprepes is a polyphagous insect that attacks over 200 varieties of plants, including commercial crops such as citrus, potato, cotton, pepper, and a number of field-grown nursery species.

The presence of Diaprepes, which is native to the Caribbean, was first documented in the U.S. in 1964 at Apopka, Orange County, Fla. Woodruff, *Ent. Cir.* 30 (Fla. Dept. Agr. & Consumer Serv., Div. Plant Ind.), 2, 1964. Since its first detection, established populations of the insect have been identified in most of Florida. Hall, *Fla. Entomol.* 78, 1173–82, 1997.

Adult Diaprepes feed on leaves of host plants and, depending on the plant type, can cause extensive damage to the foliage, causing a reduction in fruit yield or plant death.

Females lay egg clusters of approximately 100 eggs in the plant canopy. The females lay their eggs between two leaves, which they glue together to avoid predation. The glue is a mixture of long chain carbohydrates and proteins, which dries to produce a water insoluble matrix. This behavior produces a constant humidity microclimate that helps the development of the eggs. After maturation (7 to 10 days after laying), the larvae chew through the egg casings and the glue matrices and fall to the ground, where they tunnel into the soil. This subterranean larval stage is the most damaging stage to citrus trees. The larvae feed on citrus roots, which causes a reduction in fruit yield and will eventually destroy the tree.

Damage caused by the insect feeding on citrus has been estimated at $75 million per year. Diaprepes Task Force Report, Fla. Dept. Agr. & Consumer Serv., Div. Plant Ind., Bureau of Pest Eradication and Control, 1995. Damage increases each year as the coleopteran infestation spreads. This pest has affected the citrus industry in Puerto Rico to such an extent that citrus is no longer grown commercially. Due to the lack of suitable control measures, including chemical pesticides, the Diaprepes population in Florida is on the rise and poses a serious threat not only to Florida agriculture, but also to agricultural industries in other states.

Entomopathogenic fungi *Metarhizium anisopliae* and *Beauveria bassiana* capable of infecting *Diaprepes abbreviatus* larvae have been isolated and are commercially available. Quintela & McCoy, *J. Econ. Entomol.* 26, 1173–82, 1997. The fungi are primarily used as soil amendments to combat larvae already in the soil; neither of these fungi has been shown to grow on the Diaprepes eggs. The ability of these fungi to achieve significant control of the Diaprepes population is hampered by the fact that, depending on the soil titer, the Diaprepes larvae might not come into contact with the fungi. There is, therefore, a need in the art for biological reagents that can be more effectively used to combat Diaprepes infestations, as well as infestations of other Coleoptera.

SUMMARY OF THE INVENTION

It is an object of the present invention to provide compositions and methods for controlling coleopteran infestations of host plants. These and other objects of the invention are provided by one or more of the embodiments described below.

One embodiment of the invention is a purified preparation of a fungus selected from the group consisting of fungi identified with NRRL Accession Nos. 30397, 30398, 30399, 30401, 30402, 30403, and 30400 and mixtures thereof.

Another embodiment of the invention is a composition comprising a fungus selected from the group consisting of fungi identified with NRRL Accession Nos. 30397, 30398, 30399, 30401, 30402, 30403, and 30400 and spores thereof.

Still another embodiment of the invention is a method of controlling a coleopteran infestation of a host plant. The host plant is contacted with a composition comprising an egg mass pathogen. The egg mass pathogen is selected from the group consisting of fungi identified with NRRL Accession Nos. 30397, 30398, 30401, 30402, 30403, and 30400 and spores thereof. The egg mass pathogen thereby infects a coleopteran egg.

Yet another embodiment of the invention is a method of controlling a coleopteran infestation of a host plant. The host plant is contacted with a composition comprising a larval pathogen selected from the group consisting of a fungus identified with NRRL Accession No. 30399 and spores thereof. The larval pathogen infects a coleopteran larva.

Even another embodiment of the invention is a purified preparation of a first fungus or a spore thereof, wherein the first fungus has all the identifying characteristics of a second fungus selected from the group consisting of fungi identified with NRRL Accession Nos. 30397, 30398, 30399, 30401, 30402, 30403, and 30400.

Another embodiment of the invention is a purified preparation of a first fungus or a spore thereof, wherein the first fungus has all the characteristics for infection of a coleopteran egg of a second fungus selected from the group consisting of fungi identified with NRRL Accession Nos. 30397, 30398, 30401, 30402, 30403, and 30400.

Still another embodiment of the invention is a purified preparation of a first fungus or a spore thereof, wherein the first fungus has all the characteristics for infection of a coleopteran larva of a second fungus identified with NRRL Accession No. 30399.

Yet another embodiment of the invention is a composition comprising a first fungus or a spore thereof, wherein the first fungus has all the identifying characteristics of a second fungus selected from the group consisting of fungi identified with NRRL Accession Nos. 30397, 30398, 30399, 30401, 30402, 30403, and 30400.

Even another embodiment of the invention is a composition comprising a first fungus or a spore thereof, wherein the first fungus has all the identifying characteristics for infection of a coleopteran egg of a second fungus selected from the group consisting of fungi identified with NRRL Accession Nos. 30397, 30398, 30401, 30402, 30403, and 30400.

Another embodiment of the invention is a composition comprising a fungus or a spore thereof, wherein the fungus has all the identifying characteristics for infection of a coleopteran larva of a second fungus identified with NRRL Accession No. 30399.

A further embodiment of the invention is a method of controlling a coleopteran infection of a host plant. The host plant is contacted with a composition comprising a first fungus or a spore thereof. The first fungus has all the identifying characteristics for infection of a coleopteran egg of a second fungus selected from the group consisting of fungi identified with NRRL Accession Nos. 30397, 30398, 30401, 30402, 30403, and 30400.

Still another embodiment of the invention is a method of controlling a coleopteran infection of a host plant. The host plant is contacted with a composition comprising a first fungus or a spore thereof, wherein the first fungus has all the identifying characteristics for infection of a coleopteran larva of a second fungus identified with NRRL Accession No. 30399.

Another embodiment of the invention is a purified preparation of a fungus or a spore thereof. The fungus (1) is capable of infecting a coleopteran egg, whereby infection results in destruction of the egg; (2) grows rapidly on the coleopteran egg; (3) can be propagated using conventional fermentation technology; (4) sporilates easily; (5) is not pathogenic to a host plant; and (6) is not pathogenic toward beneficial insect species.

Even another embodiment of the invention is a composition comprising a fungus or a spore thereof. The fungus (1) is capable of infecting a coleopteran egg, whereby infection results in destruction of the egg; (2) grows rapidly on the coleopteran egg; (3) can be propagated using conventional fermentation technology; (4) sporilates easily; (5) is not pathogenic to a host plant; and (6) is not pathogenic toward beneficial insect species.

A further embodiment of the invention is a purified preparation of a fungus or a spore thereof. The fungus (1) is capable of infecting a coleopteran larva, whereby infection results in death of the larva; (2) can be propagated using conventional fermentation technology; (3) sporilates easily; (4) is not pathogenic to a host plant; and (5) is not pathogenic toward beneficial insect species.

Yet another embodiment of the invention is a composition comprising a fungus or a spore thereof. The fungus (1) is capable of infecting a coleopteran larva, whereby infection results in death of the larva; (2) can be propagated using conventional fermentation technology; (3) sporilates easily; (4) is not pathogenic to a host plant; and (5) is not pathogenic toward beneficial insect species.

The invention thus provides particular fungi that are pathogenic to Coleoptera. These fungi can be used to control coleopteran infestations of a wide variety of host plants.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
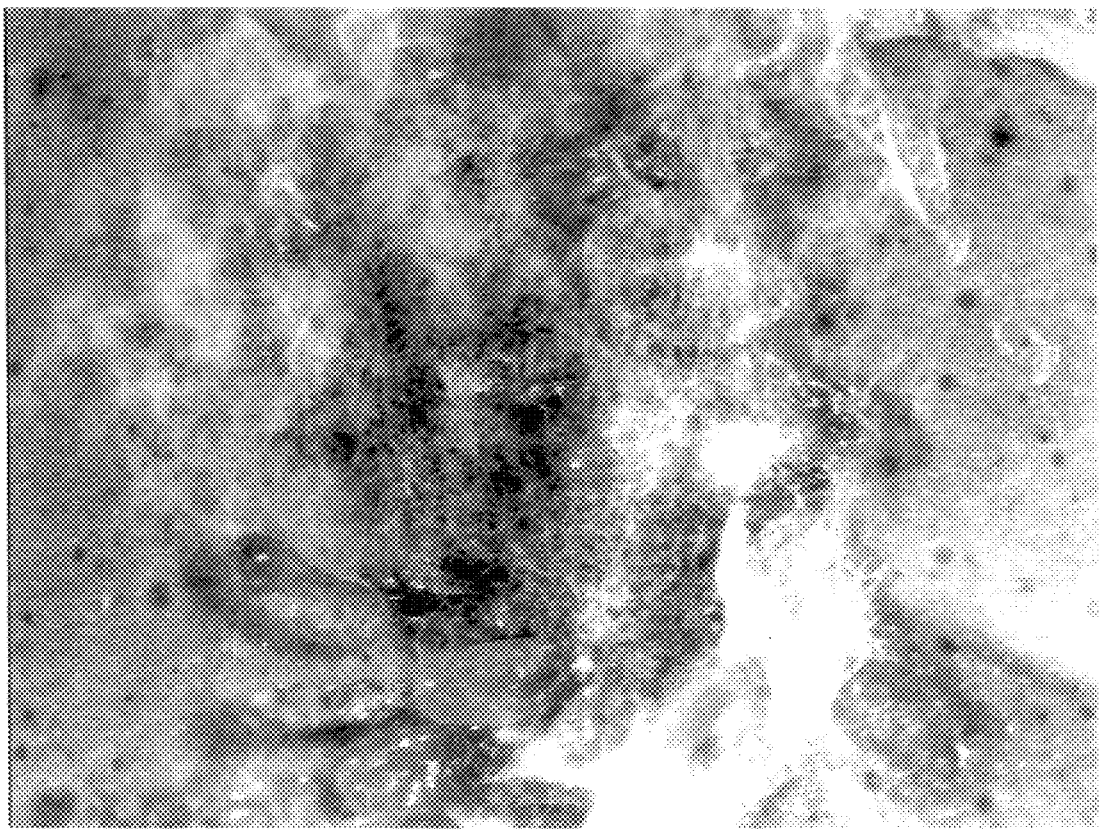
FIG. 1. NRRL 30402 infection of a Diaprepes egg mass on a citrus leaf from a grove in Indian River, Fla.

The invention provides purified preparations of distinct fungal strains, which are useful for controlling infestations of Coleoptera, particularly *Diaprepes abbreviatus*. Six of the fungal strains disclosed herein were isolated from infected Diaprepes egg clusters. These fungi are capable of colonizing the egg glue matrices, as well as the egg casings, of Coleoptera. The ability of these newly isolated fungi to grow on coleopteran egg masses permits infection of a larger number of coleopteran larvae than either of the currently available fungal species. Infection of a larger number of larvae in turn leads to more effective control of the Coleoptera population.

A seventh fungal strain, which infects larvae rather than egg masses, was isolated from infected Diaprepes larvae and also is as an effective coleopteran pathogen.

Deposits

All seven fungal strains disclosed herein were deposited on Dec. 7, 2000 to the Agricultural Research Service Culture Collection (NRRL), at the National Center for Agricultural Utilization Research Agricultural Research Service, U.S. Department of Agriculture, 1815 North University Street, Peoria, Ill. 61604, U.S.A. NRRL Accession Numbers are indicated in Table 1.

TABLE 1

| Strain | NRRL Accession No. |
| --- | --- |
| Bipolaris sp. | 30397 |
| Cladosporium sp. | 30398 |
| *Fusarium solani* | 30399 |
| Alternaria sp. | 30401 |
| Fusarium sp. | 30402 |
| Fusarium sp. | 30403 |
| Aspergillus | 30400 |

The deposits were made under conditions that assure access to the deposits during the pendency of this patent application to one determined by the Commissioner of Patents and Trademarks to be entitled to access under 37 C.F.R. §1.14 and 35 U.S.C. §122. The deposits also are available as may be required by foreign patent laws in countries in which counterparts of this application or its progeny may be filed. However, it should be understood that the availability of a deposit is not a license to practice the present invention in derogation of patent rights granted in the United States or in any foreign country.

The deposits will be stored and made available to the public in accord with the provisions of the Budapest Treaty for the Deposit of Microorganisms; i.e., they will be stored with all the care necessary to keep them viable and uncontaminated for a period of at least five years after the most recent request for the furnishing of a sample of the deposit and for a period of at least 30 years after the date of deposit or for the enforceable life of any patent which may issue disclosing the deposits. The depositor acknowledges the duty to replace a deposit should the depository be unable to furnish a sample when requested due to the condition of the deposit. All restrictions on the availability to the public of the deposits will be irrevocably removed upon the granting of a patent disclosing them.

Egg mass and larval pathogens

Laboratory experiments indicate that the spores isolated from the fungi identified with NRRL Accession Nos. 30397, 30398, 30401, 30402, 30403, and 30400 are capable of growing on the egg clusters of Coleoptera, such as *Diaprepes abbreviatus*. See FIGS. 1–8. These fungi, which are termed "egg mass pathogens," attack the glue matrices and the egg casings, which causes dehydration of the developing larvae. Death of the larvae ensues. The rate of larval growth is rapid, which causes full infection of the egg cluster before the larvae hatch. The larvae that survive to maturation come into contact with the fungi both through ingestion, because they have to cut through the egg casing the glue matrix in order to emerge, as well as dermal contact. Neonate larvae isolated from infected egg masses develop fungal infections post-emergence when compared to control groups.

Figure 9A:
FIGS. 9A and 9B. Infection of Diaprepes larva by NRRL 30399.
Figure 9B:
Figure 10A:
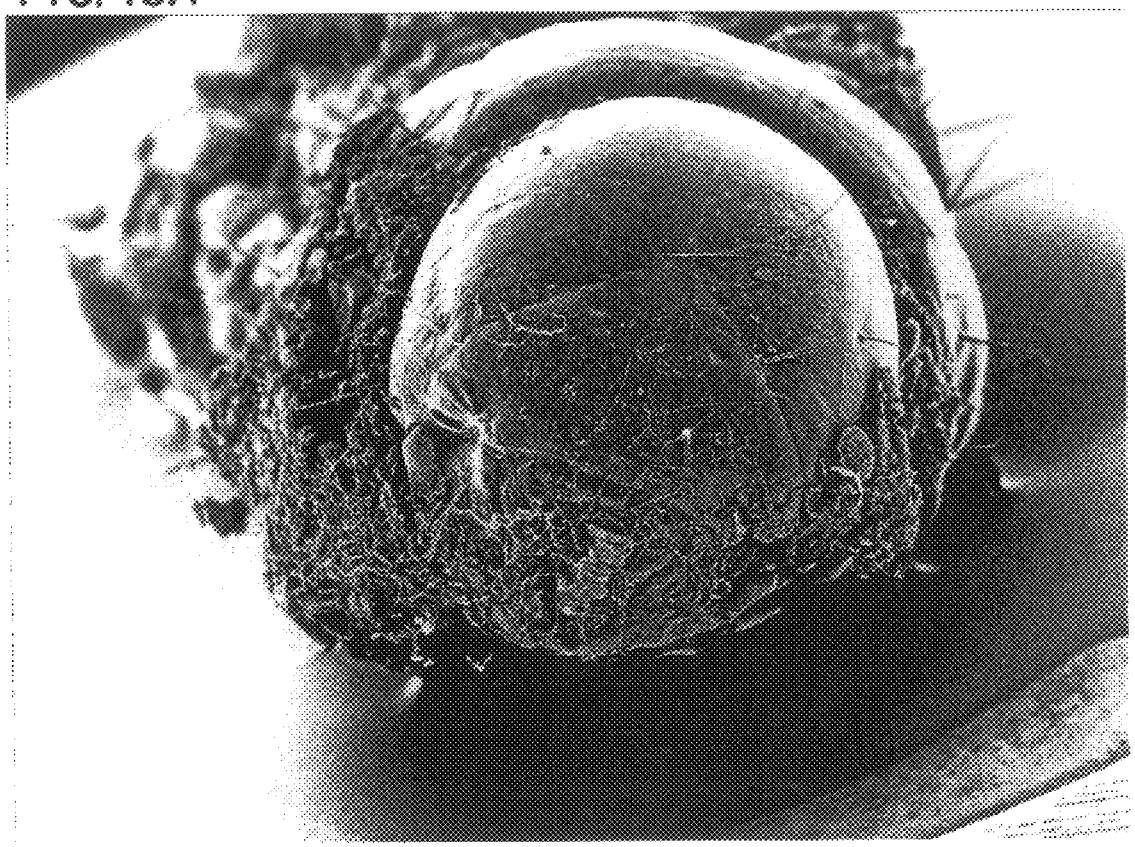
FIGS. 10A and 10B. Electron micrographs showing infection of Diaprepes larva by NRRL 30399.
Figure 10B:
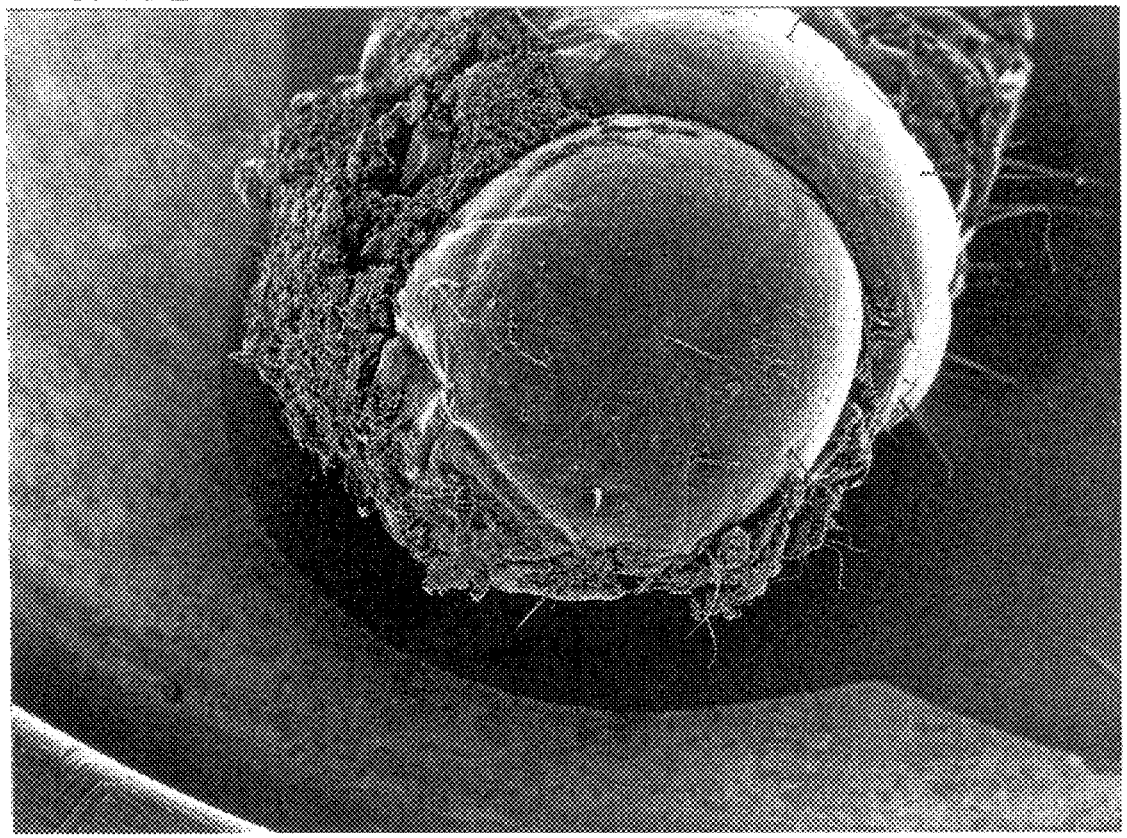
Figure 11:
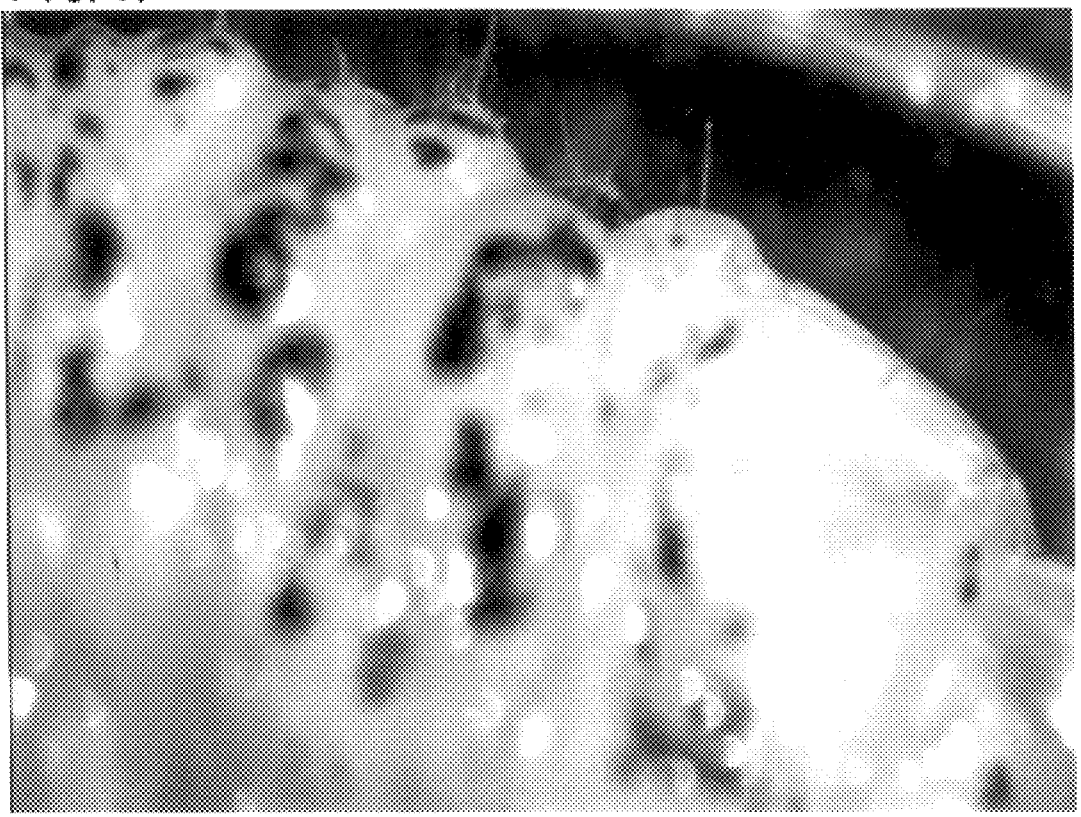
FIG. 11. Infection of mature Diaprepes larvae 72 hours post-treatment with NRRL 30399.

The fungus identified with NRRL Accession No. 30399 does not infect Diaprepes egg masses. It is, however, a potent larval pathogen. See FIGS. 9–11. This fungus exists in close association with citrus roots. The initial site of infection in the larvae occurs in the mouth and the head, indicating that infection occurs as a result of feeding. No visible phytopathogenicity has been detected in our experiments. Moreover, NRRL 30399 exhibits high levels of infectivity under low moisture levels (see Example 4, below). Thus, this pathogen provides distinct advantages compared with the two entomopathogens (*Beauveria bassiana* and *Metarhizium anisopliae*) already identified as pathogens of Diaprepes larvae.

Although initially identified as egg mass or larval pathogens of *Diaprepes abbreviatus*, fungi of the invention may be used to treat infestations of other Coleoptera, including, but not limited to, infestations of June beetles (*Phyllophaga portoricensis*), seed beetles (Bruchidae), Japanese beetles (*Popillia japonica*), handsome fungus beetles (Endomychidae), and leaf beetles (Chrysomelidae), as well as other species of weevils, such as *Parapantomorus fluctuosus, Pachnaeus litus, Pachnaeus opalus, Asynonychus godmani, Artipus floridanus, Tanymecus lacaena,* and *Epicarerus fermidolosus*. Coleopteran infestations of a variety of host plants can be treated, including, but not limited to, citrus plants, potato plants, cotton plants, pepper plants, and field-grown nursery plants (e.g., large trees, shrubs, etc.).

Methods of controlling coleopteran infestations

Egg mass pathogen spores can be produced using conventional fermentation technologies. The spores are viable as dry powder and can be provided as such for use. The dry powder can be suspended in water and applied as a foliar spray using conventional spray equipment currently in use in the citrus industry.

A concentration of $5\times10^{12}$ spores per acre (approximately $5\times10^{10}$ spores per tree in a grove of 100 trees) is preferred, although other concentrations ranging from about $5\times10^{12}$ to about $5\times10^{13}$, $5\times10^{14}$, or $5\times10^{15}$ spores per acre can be used. Optionally, spores can be provided in a composition comprising a spreader adjuvant, which is useful to reduce the effect of wind and rain in removing the spores from the foliage. Suitable spreader adjuvants have no anti-microbial activity and include products such as vegetable oil, "BOND®" (Loveland Industries, Inc., Greeley Colo.; a spreader sticker with surfactant deposition agent), and other commercially available products. Addition of such components permits an even distribution of spores on the foliage and also reduces spore loss due to wind and rain.

Preferably, egg mass pathogens are applied to the foliage of host plants before adult Coleoptera emerge. For example, adult Diaprepes begin to emerge from the soil in the early spring, after the first spring flush. However, because emergence is not synchronized and adults can emerge throughout the summer months, multiple applications of egg mass pathogens for the duration of the summer is recommended.

Larval pathogens, such as NRRL 30399, should be applied as a soil treatment. Application of larval pathogens can be accomplished using any methods known in the art, including use of a mobile sprayer or by adding larval pathogen spores to a micro-irrigation system. The recommended concentration also is $5\times10^{12}$ spores per acre, although concentrations ranging from about $5\times10^{12}$ to about $5\times10^{13}$, $5\times10^{14}$, or $5\times10^{15}$ spores per acre can be used. For soil application, there is no need to include a spreader adjuvant. Because the larval pathogen is maintained in the soil, application once every three months should provide a high level of protection.

If desired, mixtures of egg mass and/or larval pathogens can be applied to the host plant. The rate of application and/or the concentration of egg mass or larval pathogens applied can be reduced further when the insect population has reached undetectable levels. Levels of infestation can be monitored as is known in the art, for example, by visual inspection of the host plant or by collection of Coleoptera in standard ground traps.

Field data obtained through the monitoring of the field population of the pathogens indicate that the use of the most common fungicide, copper hydroxide, has little effect on the rate of pathogen infection. However, the use of such entomopathogens necessitates the prudent use of broad based fungicides currently used in citriculture.

The above disclosure generally describes the present invention. A more complete understanding can be obtained by reference to the following specific examples, which are provided for purposes of illustration only and are not intended to limit the scope of the invention.

EXAMPLE 1

Isolation Method for Entomopathogens of *Diaprepes Abbreviatus* L.

Egg mass pathogens were isolated from infected Diaprepes egg masses reared in the laboratory. Pathogens from infected egg masses were cultured on a variety of media and passaged in order to obtain pure cultures. Infectivity of the purified pathogens was checked by confirming Koch's postulate.

The following criteria were used for the isolation of egg mass pathogens:

1) ability to grow on Diaprepes egg masses;
2) ability to grow rapidly on Diaprepes egg masses (due to the short developmental time of the embryos, any possible pathogens should be able to infect a large number of eggs in relatively short time);
3) ability of the infection to destroy the eggs (i.e., superficial infection of the egg casing or the cement should not be considered as a viable infection);
4) ability to grow and be maintained easily in culture (e.g., the pathogen should be propagated using conventional fermentation technology);
5) sporilates easily (spores are easy to handle and remain viable under a variety of conditions; it is therefore crucial to isolate pathogens capable of spore formation);
6) has no pathogenic effect on beneficial insect species (to comply with EPA regulations, the infective agent should only exhibit pathogenicity towards the target insect only); and
7) has no pathogenic effect on the host citrus plant (i.e., the pathogen should not cause any kind of disease in the host citrus plant).

Following the above criteria a number of pathogens were isolated:

1) Bipolar is sp. (deposited as NRRL Accession No. 30397);
2) Cladosporium sp. (deposited as NRRL Accession No. 30398);
3) Alternaria sp. (deposited as NRRL Accession No.30401);
4) Fusarium sp. (deposited as NRRL Accession No. 30402);
5) Fusarium sp. (deposited as NRRL Accession No. 30403); and
6) Aspergillus sp. (deposited as NRRL Accession No.30400).

The identity of fungi 30397, 30398, 30401, and 30402 was confirmed morphologically and through large subunit rRNA sequence homology. The identity of fungi 30403 and 30400 was confirmed morphologically.

Spores from the isolated pathogens were brushed on wax paper and allowed to dry. See FIG. 3. The wax papers were hung in cages with mated female Diaprepes. The wax papers were incubated at 25° C. and 80% humidity for 12 days. Subsequently the egg masses were scored for infection with the pathogens.

Infection rates of 60% and higher were recorded for pathogens NRRL 30400, 30398, 30401, 30402, and 30403.

EXAMPLE 2

Spray Experiments

Spores from pathogens NRRL 30400, 30398, 30401, 30402, and 30403 were harvested and suspended in water (total spore concentration of 10,500 spores per ml). Two year-old citrus seedlings (variety Madam Vinese) were sprayed with the spore suspension to run off (approximately 100 ml). After the leaves were dry, plants were placed in cages containing 20 mating pairs of adult Diaprepes. After three days, Diaprepes were removed, and the plants were maintained for 12 days. The egg masses laid were then checked for infection. Typical infected egg masses are shown in FIGS. 4A, 4B, and 5–8. The results are reported in Table 2 ("Rep" indicates number of samples/treatment).

TABLE 2

| Treatment | Rep | Plants/ Rep | Total No. Egg Masses | No. Full Hatch | No. Infected Egg Masses | % Infection |
|---|---|---|---|---|---|---|
| Pathogen | 1 | 2 | 30 | 23 | 7 | 23 |
| Pathogen | 2 | 2 | 18 | 12 | 6 | 33 |
| Control | 1 | 2 | 8 | 8 | 0 | 0 |

EXAMPLE 3

Effect of Pathogens on Citrus Plants

Various strains of the above isolated pathogens are well known plant pathogens. To our knowledge no entomopathogenic activity has been attributed to these fungal species. It was, therefore, vital to show that the strains described above show no pathogenic activity toward citrus plants.

Various concentrations of the pathogens were applied to a variety of citrus cultivars. Foliar and root applications were made to intact plants, as well as to plants injured mechanically. Plants were maintained for two months and checked for signs of infection. None of the above described fungi showed any phytopathogenic activity. The pathogens do act as saprophytes and grow on dead brown citrus leaves. This would explain the prevalence of the fungi in citrus groves. However, due to the possible phytopathogenicity associated with these fungi, it is essential that target plants for treatment should be thoroughly tested before application of the material.

EXAMPLE 4

NRRL 30399 Exhibits High Levels of Infectivity Under Low Moisture Levels

Experiments were carried out with individual larvae maintained in 20g of dry sand containing 160,000 spores. The level of larval mortality was twice as high in pathogen treated larvae compared to controls. The results are reported in Table 3 ("Rep" indicates number of samples/treatment).

TABLE 3

| Treatment | Rep | Larvae/Rep | % Mortality |
|---|---|---|---|
| NRRL 30399 | 1 | 30 | 53 |
| NRRL 30399 | 2 | 15 | 60 |
| Control | 1 | 15 | 27 |

EXAMPLE 5

Natural Prevalence of the Egg Mass Pathogens in Florida Citrus Groves

Figure 2A:
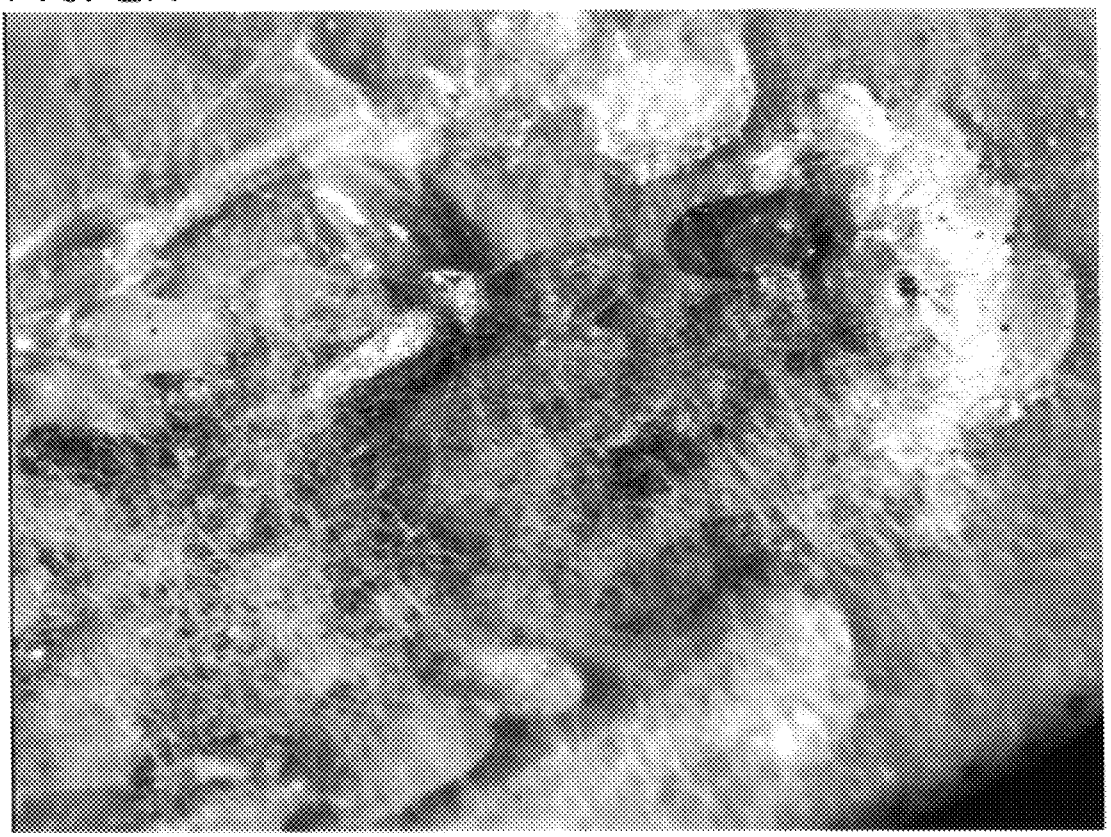
FIGS. 2A and 2B. NRRL 30401 infection of a Diaprepes egg mass on a citrus leaf from a grove in St. Lucie County, Fla.
Figure 2B:
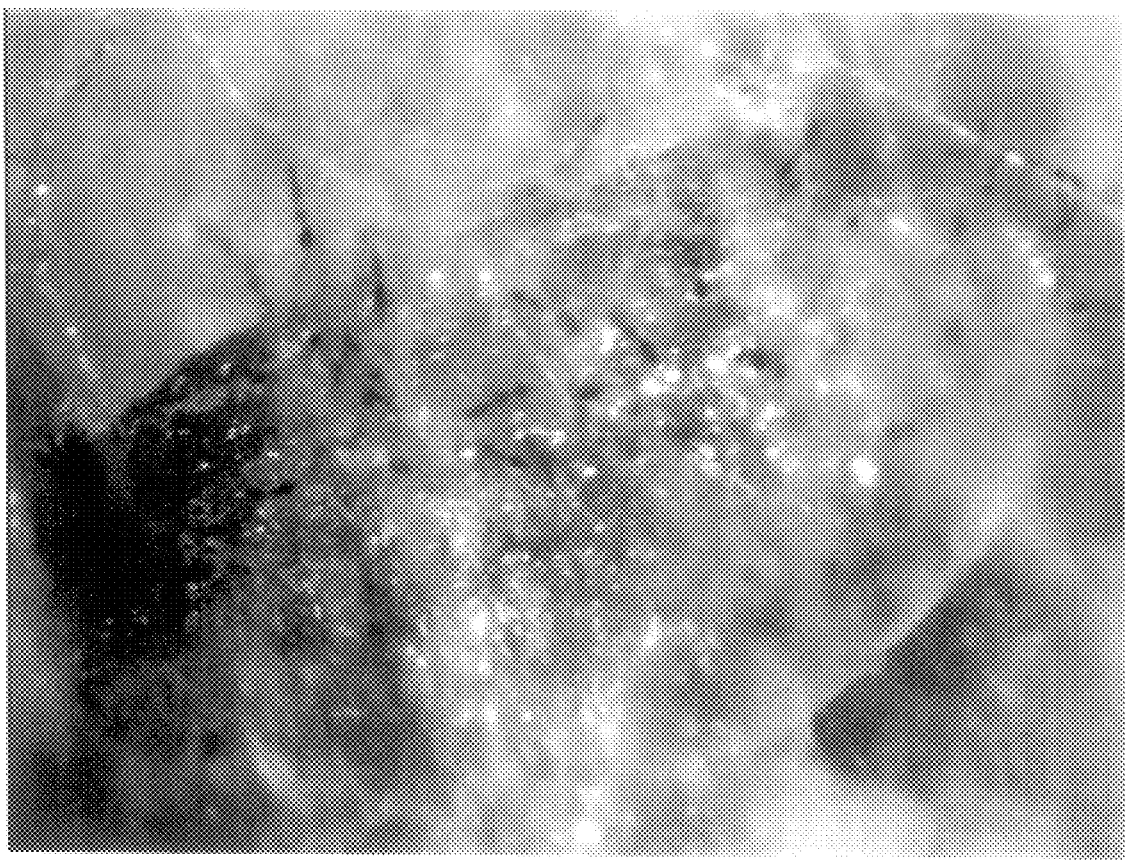
Figure 3:
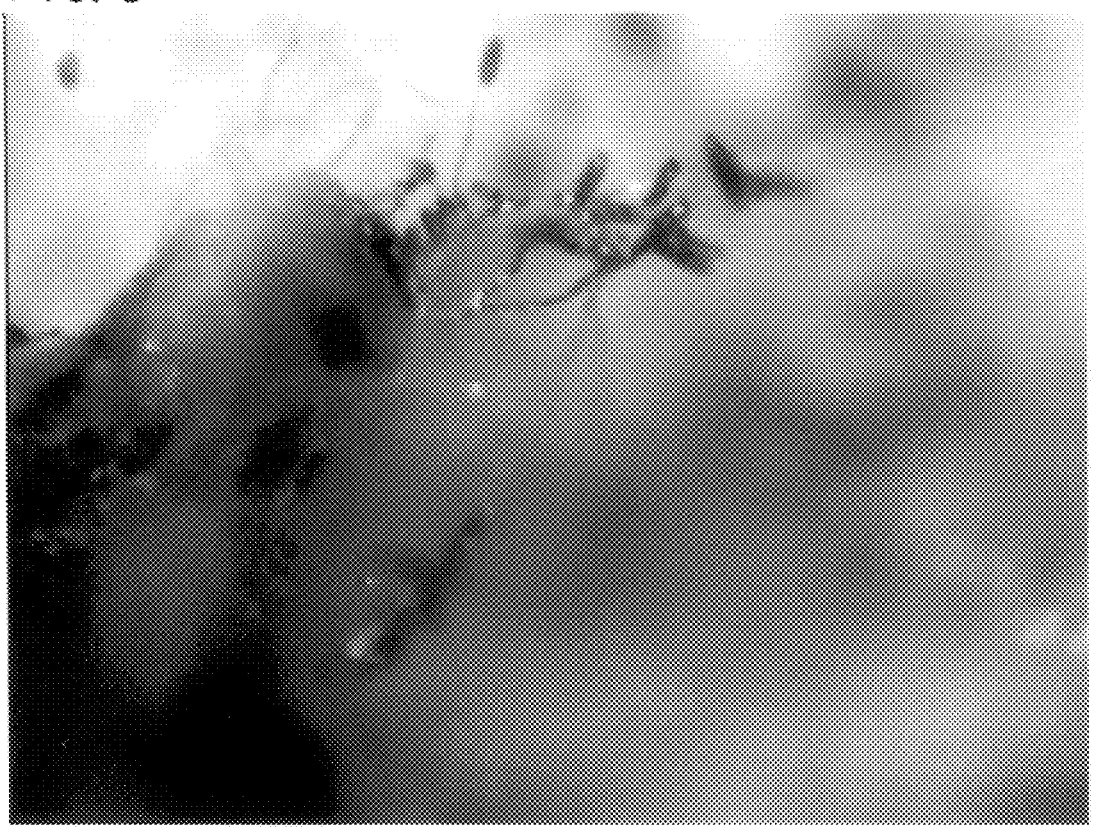
FIG. 3. NRRL 30397 growth on Diaprepes egg masses laid on wax paper.
Figure 4A:
FIGS. 4A and 4B. NRRL 30398 growth on Diaprepes egg masses laid on leaves sprayed with NRRL 30398.
Figure 4B:
Figure 5:
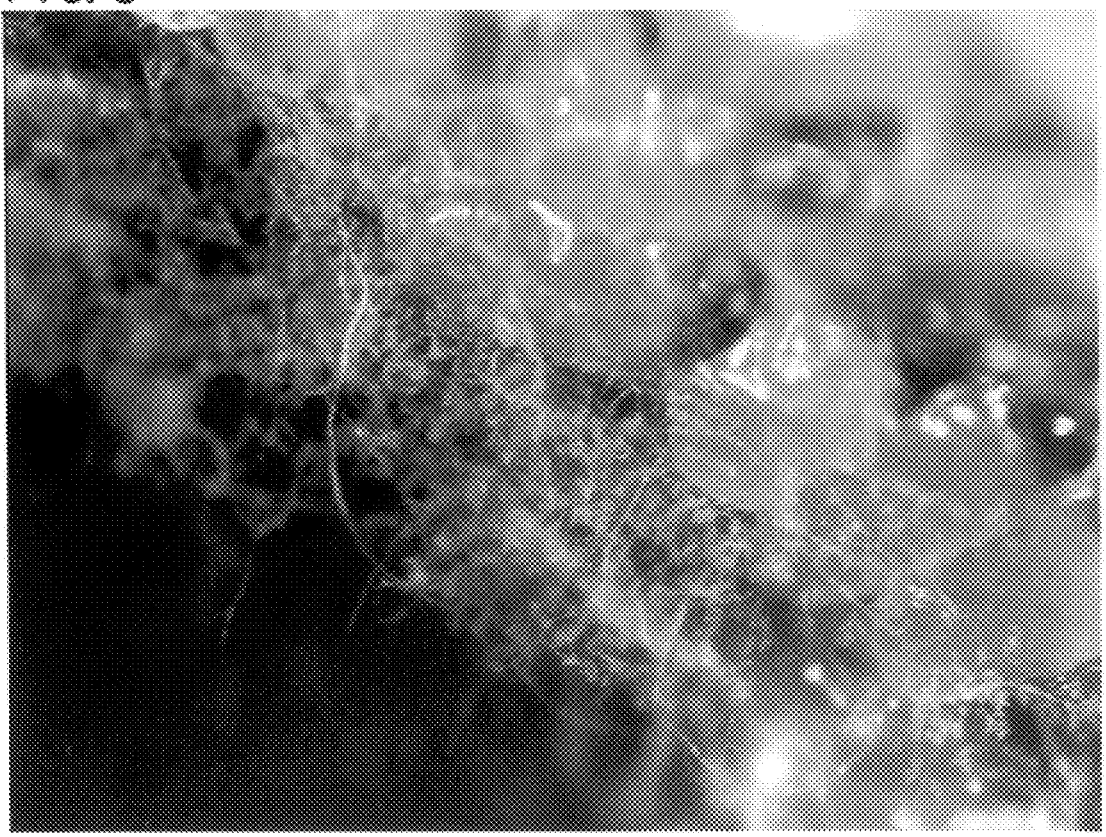
FIG. 5. NRRL 30403 growth on Diaprepes egg masses laid on leaves sprayed with NRRL 30403.
Figure 6:
FIG. 6. NRRL 30401 and 30400 growth on Diaprepes egg masses laid on leaves sprayed with NRRL 30401 and 30400.
Figure 7:
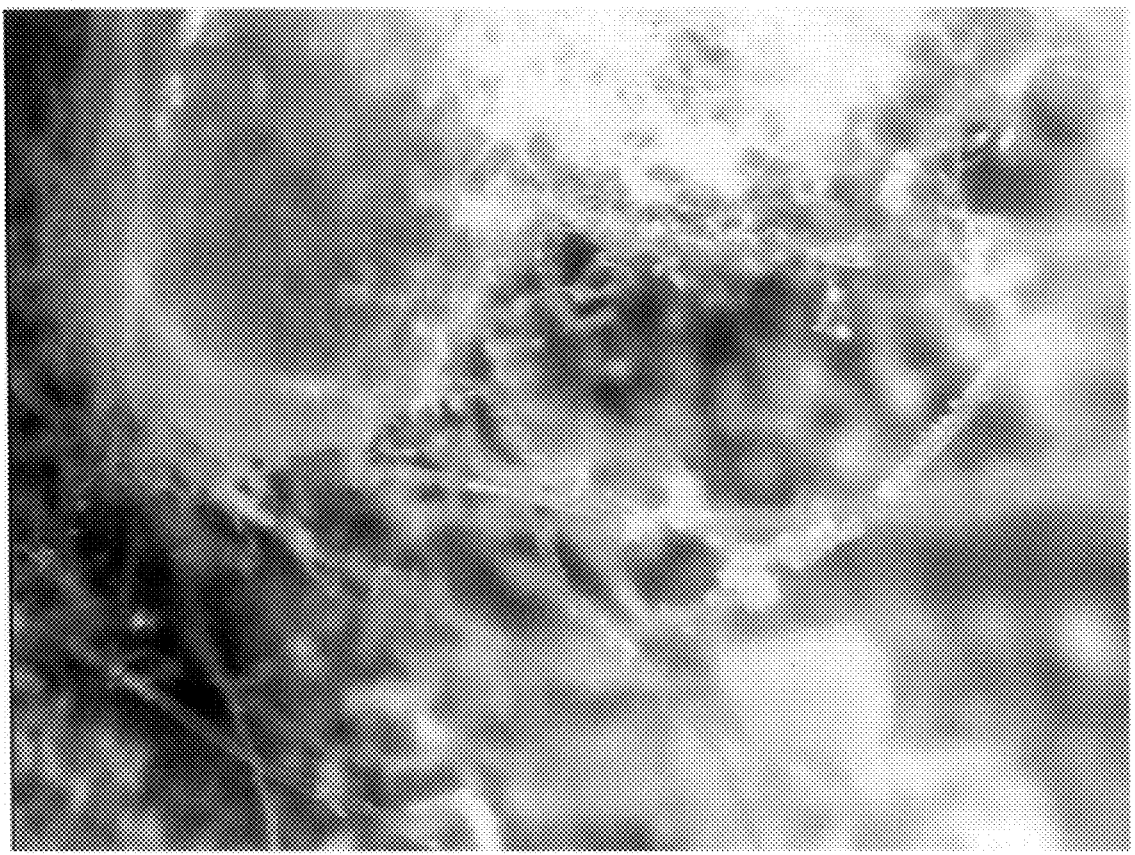
FIG. 7. NRRL 30400 growth on Diaprepes egg masses laid on leaves sprayed with NRRL 30400.
Figure 8:
FIG. 8. NRRL 30401 growth on Diaprepes egg masses laid on leaves sprayed with NRRL 30401.

A general survey of commercial citrus groves in Orange, Indian River and St. Lucie counties in Florida infested with Diaprepes was carried out. Diaprepes egg masses were checked for fungal infection. Typical egg mass infections are shown in FIGS. 1, 2A, and 2B. The survey indicated the presence of NRRL 30400, 30398, 30401, 30402, and 30403. A more detailed survey of a single citrus grove on a minimal maintenance program was carried out during August through October of 2000.

Table 4 reports the data compiled from the survey.

TABLE 4

| Date | No. Collections | Total egg mass | Infected egg mass | Full hatch egg mass | Parasitized egg mass | Infected egg mass % | Full hatch egg mass % | Parasitized egg mass % |
|---|---|---|---|---|---|---|---|---|
| 18 Aug. | 1 | 89 | 41 | 42 | 6 | 46 | 47 | 7 |
| 24 Aug. | 2 | 9 | 5 | 3 | 1 | 56 | 33 | 11 |
| 6 Sep. | 3 | 40 | 23 | 15 | 2 | 58 | 38 | 5 |
| 15 Sep. | 4 | 15 | 7 | 8 | 0 | 47 | 53 | 0 |
| 12 Oct. | 5 | 7 | 5 | 2 | 0 | 71 | 29 | 0 |
| Total | | 160 | 81 | 70 | 9 | | | |
| Total % | | | 51% | 44% | 6% | | | |

The survey indicates the prevalence of the egg mass pathogens within the wild population, which is an indication of the efficacy as well as the persistence of the pathogens under commercial grove conditions.

What is claimed is:

1. A purified preparation of a fungus or a spore thereof, wherein the fungus is selected from the group consisting of fungi identified with NRRL Accession Nos. 30397, 30398, 30401, 30400, and mixtures thereof.

2. The purified preparation of claim 1, wherein the fungus is identified with NRRL Accession No. 30397.

3. The purified preparation of claim 1, wherein the fungus is identified with NRRL Accession No. 30398.

4. The purified preparation of claim 1, wherein the fungus is identified with NRRL Accession No. 30401.

5. The purified preparation of claim 1, wherein the fungus is identified with NRRL Accession No. 30400.

6. A composition comprising a fungus or a spore thereof, wherein the fungus is selected from the group consisting of fungi identified with NRRL Accession Nos. 30397, 30398, 30401, 30400 and mixtures thereof.

7. The composition of claim 6, further comprising a spreading adjuvant.

8. The composition of claim 6, wherein the fungus is identified with NRRL Accession No. 30397.

9. The composition of claim 6, wherein the fungus is identified with NRRL Accession No. 30398.

10. The composition of claim 6, wherein the fungus is identified with NRRL Accession No. 30401.

11. The composition of claim 6, wherein the fungus is identified with NRRL Accession No. 30400.

12. A purified preparation of a first fungus or a spore thereof, wherein the first fungus has all the identifying characteristics of a second fungus selected from the group consisting of fungi identified with NRRL Accession Nos. 30397, 30398, 30401, and 30400.

13. A composition comprising a first fungus or a spore thereof, wherein the first fungus has all the identifying characteristics of a second fungus selected from the group consisting of fungi identified with NRRL Accession Nos. 30397, 30398, 30401, and 30400.

14. A method of controlling a coleopteran infestation of a host plant, comprising the step of:
contacting the host plant with a composition comprising an egg mass pathogen selected from the group consisting of fungi identified with NRRL Accession Nos. 30397, 30398, 30401, and 30400 and spores thereof, whereby the egg mass pathogen infects a coleopteran egg.

15. The method of claim 14, wherein the egg mass pathogen is the fungus identified with NRRL Accession No. 30397.

16. The method of claim 14, wherein the egg mass pathogen is the fungus identified with NRRL Accession No. 30398.

17. The method of claim 14, wherein the egg mass pathogen is the fungus identified with NRRL Accession No. 30401.

18. The method of claim 14, wherein the egg mass pathogen is the fungus identified with NRRL Accession No. 30400.

19. The method of claim 14, wherein the host plant is infested with Coleoptera selected from the group consisting of *Diaprepes abbreviatus, Parapantomorus fluctuosus, Pachnaeus litus, Pachnaeus opalus, Asynonychus godmani, Artipus floridanus, Tanymecus lacaena,* and *Epicarerus fermidolosus.*

20. The method of claim 19, wherein the Coleoptera is *Diaprepes abbreviatus.*

21. The method of claim 14, wherein the host plant is selected from the group consisting of citrus plants, potato plants, cotton plants, pepper plants, and field-grown nursery plants.

22. The method of claim 21, wherein the host plant is a citrus plant.

23. The method of claim 14, wherein the egg mass pathogen is in the form of a spore.

24. The method of claim 14, wherein the step of contacting is carried out by spraying the composition onto the host plant.

25. The method of claim 14, wherein the composition further comprises a spreading adjuvant.

26. The method of claim 14, wherein the step of contacting is carried out at least twice.

27. A method of controlling a coleopteran infection of a host plant, comprising the step of:
contacting the host plant with a composition comprising a first fungus or a spore thereof, wherein the first fungus has all the identifying characteristics for infection of a coleopteran egg of a second fungus selected from the group consisting of fungi identified with NRRL Accession Nos. 30397, 30398, 30401, and 30400.

28. The method of claim 27 wherein the second fungus is identified with NRRL Accession No. 30397.

29. The method of claim 27 wherein the second fungus is identified with NRRL Accession No. 30398.

30. The method of claim 27 wherein the second fungus is identified with NRRL Accession No. 30401.

31. The method of claim 27 wherein the second fungus is identified with NRRL Accession No. 30400.

32. The method of claim 27, wherein the host plant is infested with a Coleoptera selected from the group consisting of *Diaprepes abbreviatus, Parapantomorus fluctuosus, Pachnaeus litus, Pachnaeus opalus, Asynonychus godmani, Artipus floridanus, Tanymecus lacaena,* and *Epicarerus fermidolosus*.

33. The method of claim 32, wherein the Coleoptera is *Diaprepes abbreviatus*.

34. The method of claim 27, wherein the host plant is selected from the group consisting of citrus plants, potato plants, cotton plants, pepper plants, and field-grown nursery plants.

35. The method of claim 34, wherein the host plant is a citrus plant.

36. The method of claim 27, wherein the step of contacting is carried out by spraying the composition onto the host plant.

37. The method of claim 27, wherein the composition further comprises a spreading adjuvant.

38. The method of claim 27, wherein the step of contacting is carried out at least twice.

* * * * *